US009743942B2

(12) United States Patent
Beckman

(10) Patent No.: US 9,743,942 B2
(45) Date of Patent: Aug. 29, 2017

(54) NANOTECHNOLOGY AND OTHER SMALL SCALE INJECTABLE MACHINES WITH MULTISTAGE EXTERNAL MAGNETIC AND ELECTROSTATIC ACTUATION

(71) Applicant: Christopher V. Beckman, San Diego, CA (US)

(72) Inventor: Christopher V. Beckman, San Diego, CA (US)

( * ) Notice: Subject to any disclaimer, the term of this patent is extended or adjusted under 35 U.S.C. 154(b) by 449 days.

(21) Appl. No.: 14/217,448

(22) Filed: Mar. 17, 2014

(65) Prior Publication Data

US 2014/0343488 A1    Nov. 20, 2014

Related U.S. Application Data

(60) Provisional application No. 61/852,122, filed on Mar. 15, 2013.

(51) Int. Cl.
*A61B 17/22* (2006.01)
*A61M 5/172* (2006.01)
(Continued)

(52) U.S. Cl.
CPC ........ *A61B 17/22012* (2013.01); *A61B 17/22* (2013.01); *A61B 34/70* (2016.02);
(Continued)

(58) Field of Classification Search
CPC ........ A61M 5/172; A61B 34/73; A61B 17/22; A61B 17/22012; A61B 2017/22001; A61B 2017/22082
See application file for complete search history.

(56) References Cited

U.S. PATENT DOCUMENTS 7,643,865 B2 *   1/2010   Iddan ................. A61B 1/00156
                                                  348/77
7,857,767 B2 * 12/2010   Ferren ................. A61B 5/0084
                                                  600/300
(Continued)

FOREIGN PATENT DOCUMENTS

JP           2003325438       * 11/2003

*Primary Examiner* — Matthew F Desanto

(57) ABSTRACT

New nanotechnology and other small-scale devices for performing intravenous medical procedures are provided. In some aspect of the invention, a group of encapsulated injectable machines is delivered intravenously into a bloodstream via a syringe. A treatment area within a patient's body is specified and targeted for action by an external control system, which also monitors blood flow and other environmental. Externally applied magnetic and/or electrostatic signaling and direction devices controlled by the control system then trigger the release of encapsulation layers surrounding the injectable machines upon reaching the treatment area. The externally applied magnetic signaling and direction devices then drive the machines into treatment targets within the treatment area, exploiting an overall charge and polarity of the machines distinct from their condition during encapsulation. Pulsed magnetic fields then cause polarized moving parts within the machines to move counter to one another, with opposing angled edges breaking up the treatment target. In some embodiments, the machines may also or alternatively deliver a magnetically- or electrostatically-released medication or device to the treatment target. In still other embodiments, a local control unit within the devices may direct additional, more sophisticated actions, which actions may be directed or triggered by external signaling from the externally-applied magnetic signaling and direction devices, or other aspects of the external control system.

16 Claims, 5 Drawing Sheets

(51) Int. Cl.
  *A61B 34/00* (2016.01)
  *A61B 17/00* (2006.01)
(52) U.S. Cl.
  CPC ............ *A61B 34/73* (2016.02); *A61M 5/172* (2013.01); *A61B 2017/00017* (2013.01); *A61B 2017/00199* (2013.01); *A61B 2017/00345* (2013.01); *A61B 2017/00411* (2013.01); *A61B 2017/00876* (2013.01); *A61B 2017/22001* (2013.01); *A61B 2017/22082* (2013.01)

(56) References Cited

U.S. PATENT DOCUMENTS

| | | | | |
|---|---|---|---|---|
| 8,068,897 B1 * | 11/2011 | Gazdzinski | ........ | A61B 1/00016 600/109 |
| 8,428,685 B2 * | 4/2013 | Swain | ................ | A61B 1/00158 128/899 |
| 8,579,883 B2 * | 11/2013 | Tanaka | .............. | A61M 5/14276 604/132 |
| 9,149,617 B2 * | 10/2015 | Imran | ................ | A61M 31/002 |
| 2001/0051766 A1 * | 12/2001 | Gazdzinski | ........ | A61B 1/00016 600/309 |
| 2007/0260105 A1 * | 11/2007 | Uchiyama | .......... | A61B 1/00147 600/12 |
| 2009/0214368 A1 * | 8/2009 | Schofield | ............ | F04C 29/0021 418/1 |
| 2009/0306473 A1 * | 12/2009 | Tanaka | ................... | A61B 1/041 600/106 |
| 2011/0034766 A1 * | 2/2011 | Tanaka | ............... | A61B 1/00158 600/106 |
| 2011/0207998 A1 * | 8/2011 | Katayama | .............. | A61B 1/041 600/106 |
| 2012/0035540 A1 * | 2/2012 | Ferren | .................... | A61B 1/041 604/95.01 |
| 2013/0053767 A1 * | 2/2013 | Pivonka | ............ | A61M 25/0127 604/95.01 |
| 2014/0343488 A1 * | 11/2014 | Beckman | ......... | A61B 17/22012 604/95.01 |
| 2015/0018612 A1 * | 1/2015 | Tange | ................. | A61B 1/00158 600/109 |
| 2015/0025496 A1 * | 1/2015 | Imran | ................. | A61K 31/155 604/504 |

* cited by examiner

© 2013-2016 Christopher V. Beckman

© 2013-2016 Christopher V. Beckman

NANOTECHNOLOGY AND OTHER SMALL SCALE INJECTABLE MACHINES WITH MULTISTAGE EXTERNAL MAGNETIC AND ELECTROSTATIC ACTUATION

CROSS-REFERENCE TO RELATED APPLICATION

This application claims the benefit of U.S. Provisional Application No. 61/852,122, filed Mar. 15, 2013, the entire contents of which are hereby incorporated by reference into the present application.

Copyright and Trademark Notice: © Copyright 2013-2014 Christopher V. Beckman. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. Unless otherwise stated, all trademarks disclosed in this patent document and other distinctive names, emblems, and designs associated with product or service descriptions, are subject to trademark rights. Specific notices also accompany the drawings incorporated in this application; the material subject to this notice, however, is not limited to those drawings.

FIELD OF THE INVENTION

The present invention relates to the medical arts and nanotechnology.

BACKGROUND OF THE INVENTION

Medical devices for intravenous treatment have been in use or development for several decades, including angioplasty to treat atherosclerosis. In angioplasty, a balloon catheter is guided to a narrowed section of arteries and then expanded to widen the lumen.

Nanorobotics and other nanotechnologies have also been under development for many years, including machines that are constructed with components on a scale at or near a nanometer scale ($10^{-9}$ meters). Somewhat larger-scale machines, including nanorobots of about 10 micrometers in length, height or depth, are often defined as nanotechnology as well.

It should be understood that the disclosures in this application related to the background of the invention in, but not limited to, this section titled "Background," are to aid readers in comprehending the invention, and do not set forth prior art or other publicly known aspects affecting the application; instead the disclosures in this application related to the background of the invention comprise details of the inventor's own discoveries, work and work results, including aspects of the present invention. Nothing in the disclosures related to the background of the invention is or should be construed as an admission related to prior art or the work of others prior to the conception or reduction to practice of the present invention.

SUMMARY OF THE INVENTION

New nanotechnology and other small-scale devices for performing intravenous medical procedures are provided. In some aspect of the invention, a group of encapsulated injectable machines is delivered intravenously into a bloodstream via a syringe. A treatment area within a patient's body is specified and targeted for action by an external control system, which also monitors blood flow and other environmental. Externally applied magnetic and/or electrostatic signaling and direction devices controlled by the control system then trigger the release of encapsulation layers surrounding the injectable machines upon reaching the treatment area. The externally applied magnetic signaling and direction devices then drive the machines into treatment targets within the treatment area, exploiting an overall charge and polarity of the machines distinct from their condition during encapsulation. Pulsed magnetic fields then cause polarized moving parts within the machines to move counter to one another, with opposing angled edges breaking up the treatment target. In some embodiments, the machines may also or alternatively deliver a magnetically- or electrostatically-released medication or device to the treatment target. In still other embodiments, a local control unit within the devices may direct additional, more sophisticated actions, which actions may be directed or triggered by external signaling from the externally-applied magnetic signaling and direction devices, or other aspects of the external control system.

Canons of Construction

Where any term is set forth in a sentence, clause or statement ("statement"), each possible meaning, significance and/or sense of any term used in this application should be read as if separately, conjunctively and/or alternatively set forth in additional statements, as necessary to exhaust the possible meanings of each such term and each such statement.

It should also be understood that, for convenience and readability, this application may set forth particular pronouns and other linguistic qualifiers of various specific gender and number, but, where this occurs, all other logically possible gender and number alternatives should also be read in as both conjunctive and alternative statements, as if equally, separately set forth therein.

DETAILED DESCRIPTION OF THE INVENTION

Figure 1:
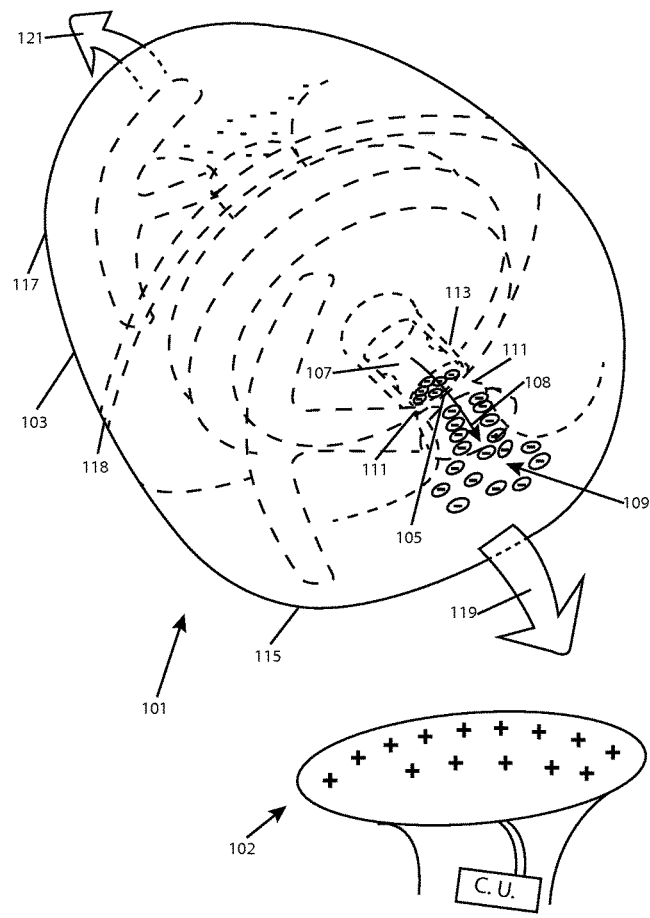
FIG. 1 is a perspective view depicting an exemplary injectable machine and an external magnetic and/or electrostatic signaling and direction device controlling activity of the injected machine, in accordance with aspects of the present invention.

FIG. 1 is a perspective view depicting an exemplary injectable machine 101 and an externally applied magnetic and/or electrostatic signaling and direction device 102 controlling activity of injectable machine 101, in accordance with aspects of the present invention. Injectable machine 101 comprises an outer protective capsule 103, which may be actuated by the application of a magnetic and/or electrostatic field. Specifically, by applying a positive electrostatic charge, or the positive pole of a magnetic dipole, proximate to a negatively charged locus 105 of machine 101, a slidable cylinder 107 is pulled outward against a negative locus 109 of capsule 103, as demonstrated by motion arrow 108. Locking tabs 111 on the inner surface of cylinder-holding shaft 113 (in which cylinder 107 traveled in reaction to the positive field created by external device 102) then hold cylinder 107 in a position against locus 109. Because both locus 109 and 105 are negatively charged, a repulsive force is generated between them. The amount of this force is sufficient to overcome the forces of friction, attractive forces, structural connections, hydrogen bonding, or other forces holding capsule 103 together and, as a result, capsule halves 115 and 117 separate along a joint 118, and release the remainder of machine 101, as shown by capsule separation motion arrows 119 and 121. In some embodiments, an additional, opposing external device applies a similar external electrostatic or magnetic force (but, in some embodiments, with reversed charge or polarity, addressing reversed charges in corresponding loci of the opposing side of machine 101). As will be shown in greater detail below, external device 102 preferably is present on the outside of a treatment area, but creates electrostatic or magnetic fields, and field pulses, of sufficient strength to cause the separation, and other machine actuation discussed in this application, for example, in the following figures. In some aspects of the present invention, fixed magnetic and electrostatic dipoles and charges are present in machines such as 101, and differential charges and dipoles may be present in and between subfeatures, which then may be externally actuable, for example, by an externally applied magnetic and/or electrostatic signaling and direction device such as 102. In other embodiments, such charges and dipoles may be influenced by and altered by, or moved by, such external magnetic or electrostatic field-generating devices, and then further controlled by subsequently-generated magnetic or electrostatic fields. In this way, and in other ways discussed in greater detail below, actuation of particular sub-mechanisms of a machine, such as 101, may be turned on or turned off.

Figure 2:
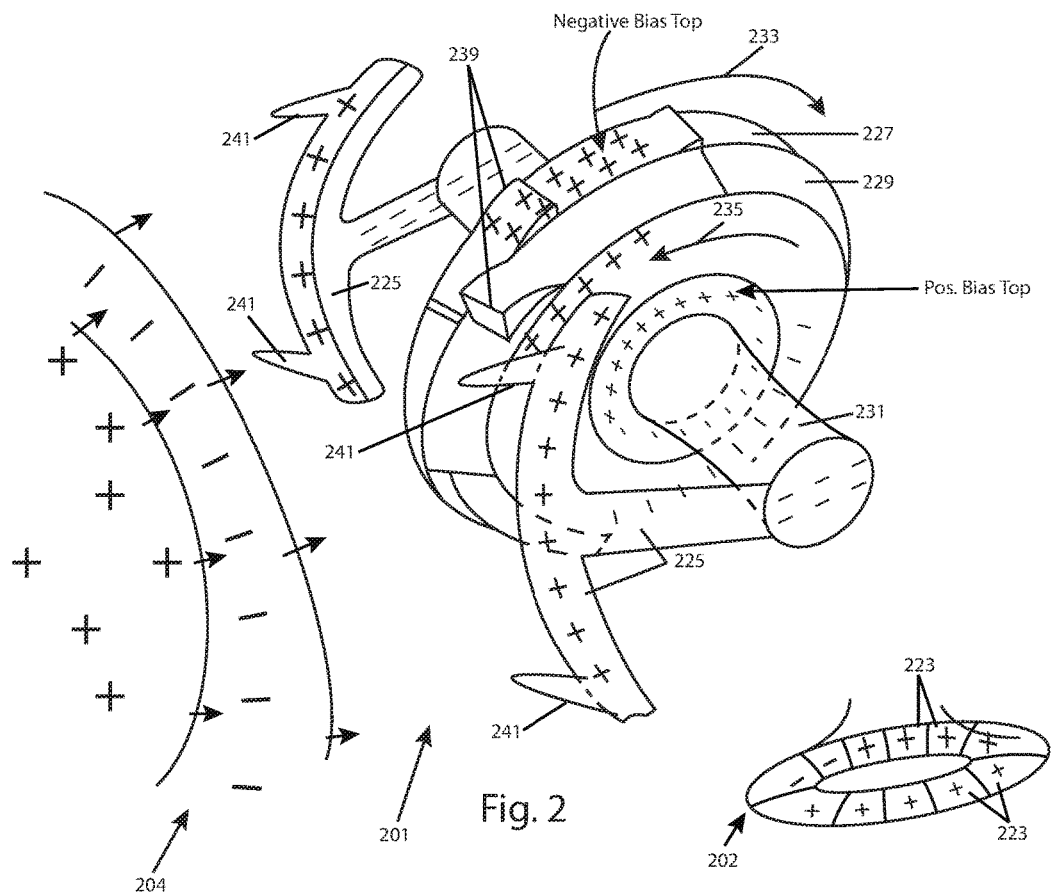
FIG. 2 is a perspective view depicting aspects of the same exemplary injectable machine and external device depicted in FIG. 1, above, but in which the injectable machine has been stripped of a protective capsule for deployment in a treatment area.

FIG. 2 is a perspective view depicting aspects of the same exemplary injectable machine, now 201, and external device, now 202, depicted in FIG. 1, above, but in which the injectable machine has been stripped of a protective capsule for deployment in a treatment area. Machine 201 has an overall positive electrostatic charge, or outer positive pole, and, as a result, externally applied magnetic and/or electrostatic signaling and direction device 202 is able to move machine 201 to desired regions of space within a sufficient proximity to both machine 201 and device 202. Device 202 does so by creating electrostatic and magnetic fields via separately chargeable regions, 223. For example, by creating a negative electrostatic or magnetic charge in leftward regions, but a positive charge in rightward regions 223 of device 202, device 202 may drive the positively-charged arms 225 of machine 201 to the left and turn machine 201 counterclockwise (in the perspective of the figure). To further aid in controlling the location of machine 201, and driving it into a desired region, a second externally applied magnetic and/or electrostatic signaling and direction device 204 may also be used. Device 204 may be larger, and able to create greater pulling or pushing force with respect to charged arms 225, while device 202 is used predominantly for steering machine 201 (or another or a group of other, similar charged machines). The two devices 202 and 204 may also be used to reinforce a magnetic or electrostatic field, or fields, for example, by exerting opposing magnetic or electrostatic dipoles or charges from opposing points surrounding a treatment area. But, in some embodiments, a single such arm is used.

Devices 202 and 204 may be pulsed or otherwise create waves and other patterns of changing magnetic and/or electrostatic fields to create and power rotary and other actions of tools and toolsets within device 201. In more detail, two spinning saw disks, 227 and 229 are a able to independently, and opposingly, rotate about an axel 231, as shown by opposing rotary motion arrows 233 and 235. For example, each disk 227 and 229 may comprise a drivable dipole 237 that may vary at different areas of each disk. To drive each disk in opposite directions, a wave or other pattern in magnetic fields generated by either or both of devices 202 and 204 (for example, by pulsed magnetic regions 223) may vary in opposing directions by distances below the sizes of disks 227 and 229, or charged features within them. In this way, the waves or other patterns, if strong enough, can override any tendency of the dipoles of disks 227 and 229 to lock with one another. Other local charges or dipoles, for example, dipole 237, may also oppose the dipoles of one or both disks 227 and 229, and drive them countering the tendency to lock. In some embodiments, axel 231, or a surrounding bushing, may be fixed in rotation with one, but not both, of disks 227 or 229, and may have a dipole opposing the dipole of the disk with which it is fixed, but which dipole is also located closer to the other disk. In this way, a wavefront or other magnetic or electrostatic field feature that reaches the other disk and axel dipole (but not yet the disk fixed to the axel) will drive them to rotate in opposing directions. To drive counter-rotation in a particular direction—for example to push chipping teeth 239 toward a target, as shown by motion arrows 233 and 235, a magnetic field may generally force machine 201 into a locked position, but strong, temporary waves or sub-currents may still be used to differentially drive the rotation of disks 227 and 229. In some embodiments, gripping features such as claws 241 may allow machine 201 to first be driven into a target, for example, with a strong negative charge or pole facing arms 225, and, once fixed in place, a second phase of magnetic waves may drive the counter-rotation of disks 227 and 229.

Figure 3:
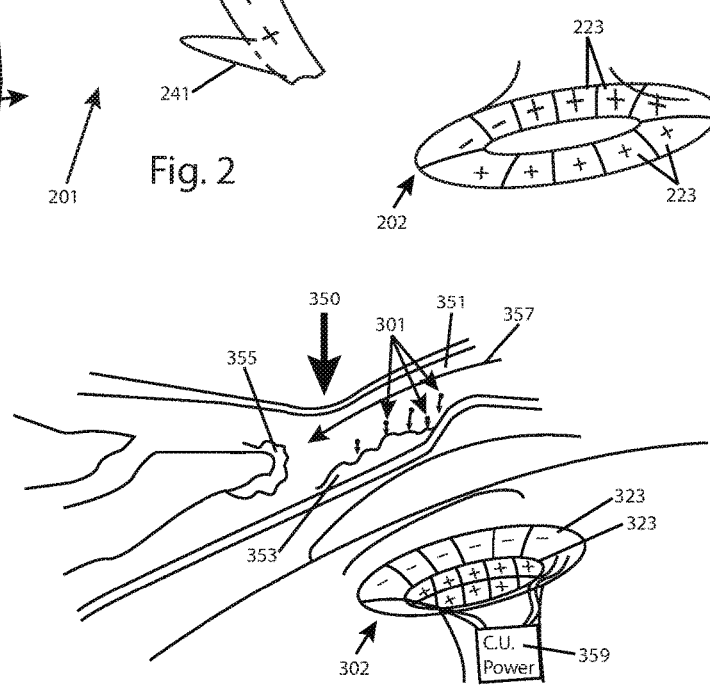
FIG. 3 is a cross-section of a treatment area, specifically a branched blood vessel with a atherosclerotic plaques, including a group of injected machines, such as the injectable machines set forth in reference to FIGS. 1 and 2, above, and an externally applied magnetic and/or electrostatic signaling and direction device controlling activity of the injected machines.

FIG. 3 is a cross-section of a treatment area 350, specifically a branched blood vessel 351 with a atherosclerotic plaques 353 and 355, including a group of injected machines 301, which may be similar in nature to the injectable machines set forth in reference to FIGS. 1 and 2, above. FIG. 3 also depicts and an externally applied magnetic and/or electrostatic signaling and direction device 302 controlling activity of the injected machines 301. Vessel 351 contains a stream of blood pulsed in a direction generally depicted by blood flow arrow 357. Machines 301 have been injected into the lumen of vessel 351 at a position upstream (not pictured) from plaques 353 and 355. As such, blood flow has brought machines 301 generally into the treatment area. As they are brought into the treatment area by the blood flow, device 302 begins to direct them further, and at a vector that, combined with the force of the blood flow, causes them to arrive by a net vector at a location (and, preferably, at distributed or purposeful cutting locations) of one of plaques 353 or 355. In the example provided, machines 301 are shown being forced by electrostatic fields created by device 302 into distributed locations about plaque 353. Device 302 is shown at an external location, nearby the treatment area. In some embodiments, chargeable, directable arms, streamlined for insertion, may also be injected into a patient's body, to aid in directing machines 301, but, preferably, device 302 is present entirely outside of the patient's body in which the treatment area is found, for minimal invasion. To aid in controlling the magnetic and electrostatic machine-directing and actuating fields, a control unit 359 may be connected with, power and control device 302. In some embodiments, the locations, or concentrations of machines 301 may be detected by the control system, and altered in real time to obtain destinations, and actuation in a more precise location desired. A wide variety of real-time scanning and location hardware both in control unit 359 and within machines 301 (for example, identifiable reflecting beacons within machines 301 transponding with electromagnetic signals from an antenna within control unit 301) in conjunction with medical imaging devices, may be used for this tracking purpose. Such imaging devices may also be able to track the progress of effects, such as plaque breakdown, of the use of machines 301, and arrest their action at a desired time of successful procedure completion.

Machines 301 may be equipped with a wide variety of tools, in addition to or rather than, capsule 115/117, and rotary chopping disks such as 227 and 229. For example, in some embodiments, machines 301 may comprise a vector for implantation or injection at a desired site—such as a die, radiotherapy pellets, or other medicines.

In some embodiments, injectable machines 301 may also comprise a control unit, for example, controlling actuators, tools and communications hardware present within machines 301. In such embodiments, control unit 359 may issue and receive commands and other communications from and to machines 301. However, at present, due to the size constraints of control units comprising processors and other computer hardware within injectable machines, the remote signal-induced actuation, powering and control of actuators, as set forth in greater detail in this application, are presently preferred. However, it should be understood that any of the actuation, monitoring and other actions of the present invention may also, alternatively, take place with the assistance of on-board control and communications hardware, sensors and actuators, of the nature found in larger-scale robotics.

Figure 4:
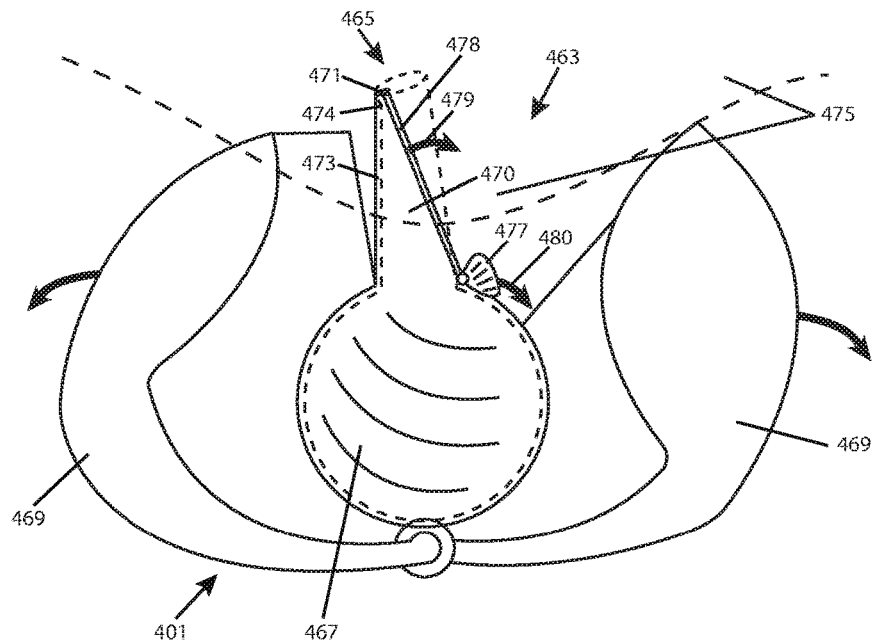
FIG. 4 is a perspective view of another exemplary injectable machine, comprising a new form of contact-driven medicine deployment mechanism.

FIG. 4 is a perspective view of another exemplary injectable machine 401, comprising a new form of contact-driven medicine deployment mechanism 463. Specifically, medicine deployment mechanism 463 comprises a contact-opening needle 465 and a pressurized fluid container 467. Initially, and prior to full deployment, machine 401 may be encapsulated by capsule halves 469. However, when deployed, differential charged regions or dipoles within capsule halves 469 may cause them to open in reaction to an exerted magnetic or electrostatic field, in a manner similar to that discussed with reference to FIG. 1 and capsule halves 115 and 117. However, the separation of capsule halves 469 may be temporary, and reversed by, for example, a spring or other force bias tending to close halves 469 when not under the influence of such a magnetic field.

When closed, halves 469 create a capsule enclosing and protecting needle 465. When opened, as pictured, needle 465 does not immediately dispense the contents of fluid container 467. Instead, an elastomeric material 470 comprised in needle 465 causes needle 465 to maintain a seal closing needle hole 471, and sealing in the contents of fluid container 467. Needle 465 is especially sharp in this closed condition, however, and comprises at least one thin, stiff structural member 473, preferable with a sharp point 474. Thus, with capsule halves 469 spread open (as pictured) and needle 465 exposed, if machine 401 collides with a tissue or other material, such as may be present in the tissue area shown as 475, needle 465 may pierce tissue in area 475. As this occurs, the outer surface 476 of the tissue will press against a wide opening lever pad 477, causing it and a lever 478 within needle 465 to pivot, as shown by pivoting motion arrows 479 and 480, pulling open elastomeric material 470 and needle hole 471. At that point, pressurized fluid within container 467 is expelled into the lower pressure of the tissue in area 475, treating it with that fluid. The fluid present in container 467 may be any of a wide variety of possible medical deliverables, such as, but in no way limited to, small molecule medicines, biologics and tags.

A wide variety of self-deploying, or contact-deploying mechanisms, in addition to or other than the mechanism set forth with reference to FIG. 4 may also be used. For example, another such form of contact-deploying medicinal machines is provided below, with reference to FIG. 7.

Figure 5:
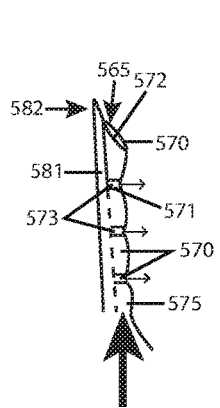
FIG. 5 is a side view of aspects of a new form of low-profile injection-opening medical needle, in accordance with aspects of the present invention, shown in a closed (unpressurized) state.

FIG. 5 is a side view of aspects of a new form of low-profile injection-opening hollow medical needle 565, in accordance with aspects of the present invention, shown in a closed (unpressurized) state. Once again, as discussed in with needle 465 of FIG. 4, an elastomeric material 570 is shown in the figure, which tends to hold needle 565 in a closed position (not allowing the release of a pressurized fluid. In the instance of needle 565, however, bands of elastomeric material, such as the examples shown as 573, are shown, which close off an inner lumen 575 of needle 565. Needle 565 may be opened by a wide variety of mechanisms but, preferably, an increase in pressure overcomes the elastomeric inward force of material 570 and bands 573, causing the expansion of lumen 575/675, as shown in FIG. 6, below.

Figure 6:
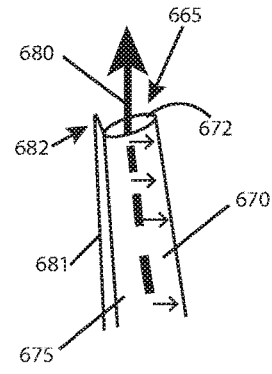
FIG. 6 is a side view of aspects of the same form of low-profile injection-opening medical needle, in accordance with aspects of the present invention, shown in an open (pressurized) state.

FIG. 6 is a side view of aspects of the same form of low-profile injection-opening hollow medical needle, now 665, in accordance with aspects of the present invention, shown in an open (pressurized) state. As mentioned above, if a fluid of sufficient pressure is pushed into the lumen (now 675) of needle 665, the elastomeric material, now 670, will yield to that pressure and permit the expulsion of the fluid from needle 665, through an expanded, now higher profile loop 672, composed of elastomeric material 670. Thus, showing that expansion and fluid pressure, the present figure depicts fluid flow according to a fluid flow direction arrow 680, as well as the widened elastomeric material 670. The great pressure of the fluid being expelled causes a maximum lumen size to be obtained but, preferably, no further due to the stretching limit of material 670 and the elastomeric bands 573 (which virtually disappear from view when material 670 is stretched to its maximum.

A sharp, rigid inner needle support member 681, with a sharp tip 682, allows needle 665 to operate by piercing tissue regardless of whether elastomeric material 570/670 is expanded by expelling fluid. In fact, the lower overall size and profile of needle 665 may make its use during piercing less painful by interfering with fewer nerves.

Figure 7:
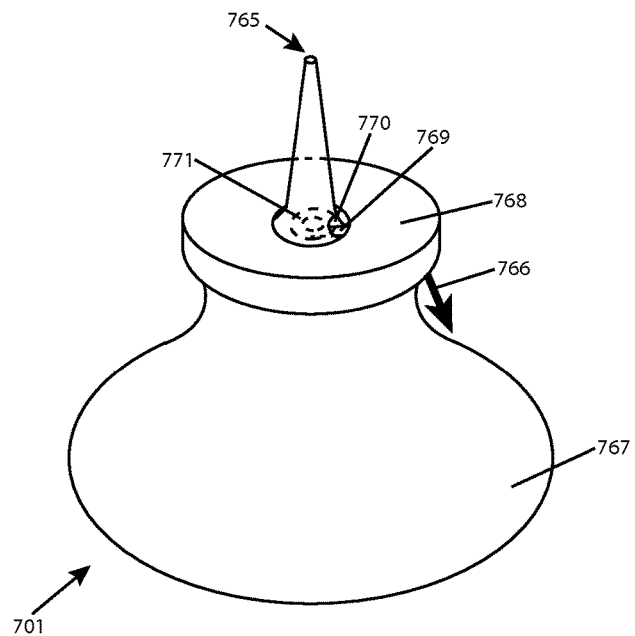
FIG. 7 is a perspective view of another form of contact-driven medicine deployment mechanism, in accordance with aspects of the present invention.

FIG. 7 is a perspective view of another form of contact-driven medicine deployment mechanism 701, in accordance with aspects of the present invention. Again a hollow needle 765 is shown, along with a pressurized fluid container 767. A pressable ring 768 is also present, and, when needle 765 is sufficiently pressed into tissue, is pushed in the direction shown by motion arrow 766. An attached tab 769 within a sealed slot 770 then also travels downward and, because another end of tab 769 is attached to a stopper 771, stopper 771 also descends and releases the pressurized fluid from container 767.

Figure 8:
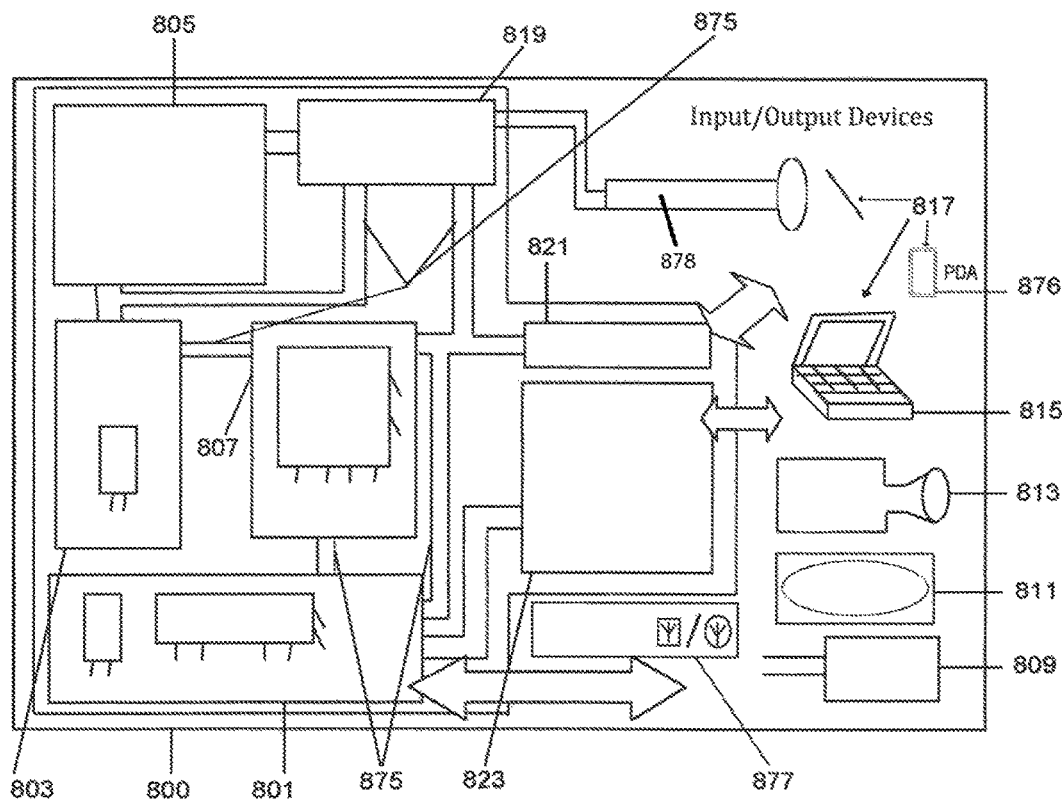
FIG. 8 is a schematic block diagram of some elements of an exemplary control system that may be used in accordance with aspects of the present invention.

FIG. 8 is a schematic block diagram of some elements of an exemplary control system 800 that may be used in accordance with aspects of the present invention, such as, but not limited to implementing data storage and supplementation. The generic and other components and aspects described herein are not exhaustive of the many different systems and variations, including a number of possible hardware aspects and machine-readable media that might be used, in accordance with the present invention. Rather, the system 800 is described to make clear how aspects may be implemented. Among other components, the system 800 includes an input/output device 801, a memory device 803, storage media and/or hard disk recorder and/or cloud storage port or connection device 805, and a processor or processors 807. The processor(s) 807 is (are) capable of receiving, interpreting, processing and manipulating signals and executing instructions for further processing and for output, pre-output or storage in and outside of the system. The processor(s) 807 may be general or multipurpose, single- or multi-threaded, and may have a single core or several processor cores, including, but not limited to, microprocessors. Among other things, the processor(s) 807 is/are capable of processing signals and instructions for the input/output device 801, analog receiver/storage/converter device 819, analog in/out device 821, and/or analog/digital or other combination apparatus 823 to cause a display, light-affecting apparatus and/or other user interface with active physical controls, such as indicator buttons and displays, and control actuation monitoring hardware, any of which may be comprised or partially comprised in a GUI, to be provided for use by a user on hardware, such as a specialized personal computer, media console, monitor or PDA (Personal Digital Assistant) or control unit screen (including, but not limited to, monitors or touch- and gesture-actuable displays) or a terminal monitor with a mouse and keyboard or other input hardware and presentation and input software (as in a software application GUI), and/or other physical controls, such as a button, knob or LEDs for determining appliance conditions or statuses or related circuit or other characteristics. Alternatively, or in addition, the system, using processors 807 and input/output devices 819, 821 and/or 823, may accept and exert passive and other physical (e.g., tactile) user, power supply, appliance operation, user activity, circuit and environmental input (e.g., from sensors) and output.

For example, and in connection with aspects of the invention discussed in reference to the remaining figures, the system may carry out any aspects of the present invention as necessary with associated hardware and/or using specialized software, including, but not limited to, controlling electric or magnetic fields to direct and actuate nanomachines and other small, injectable machines. The system may also, among many other things described for control systems in this application, respond to user, sensor and other input (for example, by a user-actuated GUI controlled by computer hardware and software or by another physical control) to issue alerts, alter settings, control data storage, correction, augmentation and supplementation, or perform any other aspect of the invention requiring or benefiting from use of a control system. The system 801 may communicate with another control system, similar in nature to system 801, and control and be controlled by such a control system, and may permit the user and/or system-variation of settings, including but not limited to the affects of user activity and usage history on modes of operation of the system, and send external alerts and other communications (for example, to users or other administrators) via external communication devices, for any control system and control unit aspect that may require or benefit from such external or system-extending communications.

The processor(s) 807 is/are capable of processing instructions stored in memory devices 803 and/or 805 (and/or ROM or RAM), and may communicate with any of these, and/or any other connected component, via system buses 875. Input/output device 801 is capable of input/output operations for the system, and may include/communicate with any number of input and/or output hardware, such as a computer mouse, keyboard, entry pad, actuable display, networked or connected second computer or processing device, control unit, other GUI aspects, camera(s) or scanner(s), sensor(s), sensor/motor(s), actuable electronic components (with actuation instruction receiving and following hardware), RF antennas, other radiation or electrical characteristics reading, monitoring, storage and transmission affecting hardware, as discussed in this application, range-finders, GPS systems, receiver(s), transmitter(s), transceiver(s), transflecting transceivers ("transflecters" or "transponders"), antennas, electromagnetic actuator(s), mixing board, reel-to-reel tape recorder, external hard disk recorder (solid state or rotary), additional hardware controls (such as, but not limited to, buttons and switches, and actuators, current or potential applying contacts and other transfer elements, light sources, speakers, additional video and/or sound editing system or gear, filters, computer display screen or touch screen. It is to be understood that the input and output of the system may be in any useable form, including, but not limited to, signals, data, commands/instructions and output for presentation and manipulation by a user in a GUI. Such a GUI hardware unit and other input/output devices could, among other things, implement a user interface created by machine-readable means, such as software, permitting the user to carry out any of the user settings, commands and input/output discussed above, and elsewhere in this application.

801, 803, 805, 807, 819, 821 and 823 are connected and able to communicate communications, transmissions and instructions via system busses 875. Storage media and/or hard disk recorder and/or cloud storage port or connection device 805 is capable of providing mass storage for the system, and may be a computer-readable medium, may be a connected mass storage device (e.g., flash drive or other drive connected to a U.S.B. port or Wi-Fi) may use back-end (with or without middle-ware) or cloud storage over a network (e.g., the internet) as either a memory backup for an internal mass storage device or as a primary memory storage means, and/or may be an internal mass storage device, such as a computer hard drive or optical drive.

Generally speaking, the system may be implemented as a client/server arrangement, where features of the invention are performed on a remote server, networked to the client and facilitated by software on both the client computer and server computer. Input and output devices may deliver their input and receive output by any known means of communicating and/or transmitting communications, signals, commands and/or data input/output, including, but not limited to, input through the devices illustrated in examples shown as 817, such as 809, 811, 813, 815, 876 and 877 and any other devices, hardware or other input/output generating and receiving aspects—e.g., a PDA networked to control a control unit with the aid of specialized software (a.k.a. a "PDA Application" or "App."). Any phenomenon that may be sensed may be managed, manipulated and distributed and may be taken or converted as input or output through any sensor or carrier known in the art. In addition, directly carried elements (for example a light stream taken by fiber optics from a view of a scene) may be directly managed, manipulated and distributed in whole or in part to enhance output, and radiation or whole ambient light or other radio frequency ("RF") information for an environmental region may be taken by a photovoltaic apparatus for battery cell recharging, or sensor(s) dedicated to angles of detection, or an omnidirectional sensor or series of sensors which record direction as well as the presence of electromagnetic or other radiation. While this example is illustrative, it is understood that any form of electromagnetism, compression wave or other sensory phenomenon may become such an "ambient power" source harnessed to power the operations of a control unit and/or control system and/or may include such sensory directional and 3D locational or other operations-identifying information, which may also be made possible by multiple locations of sensing, preferably, in a similar, if not identical, time frame. The system may condition, select all or part of, alter and/or generate composites from all or part of such direct or analog image or other sensory transmissions, including physical samples (such as DNA, fingerprints, iris, and other biometric samples or scans) and may combine them with other forms of data, such as image files, dossiers, appliance-identifying files, or operations-relevant recordings, or metadata, if such direct or data encoded sources are used.

While the illustrated system example 800 is helpful to understand the implementation of aspects of the invention, it should be understood that any form of computer system may be used to implement many control system and other aspects of the invention—for example, a simpler computer system containing just a processor (datapath and control) for executing instructions from a memory or transmission source. The aspects or features set forth may be implemented with, as alternatives, and/or in any combination, digital electronic circuitry, hardware, software, firmware, or in analog or direct (such as electromagnetic wave-based, physical wave-based or analog electronic, magnetic or direct transmission, without translation and the attendant degradation, of the medium) systems or circuitry or associational storage and transmission, any of which may be aided with enhancing media from external hardware and software, optionally, by wired or wireless networked connection, such as by LAN, WAN or the many connections forming the internet or local networks. The system can be embodied, in part, in a tangibly-stored computer program, as by a machine-readable medium and propagated signal, for execution by a programmable processor. The method steps of the embodiments of the present invention also may be performed by such a programmable processor, executing a program of instructions, operating on input and output, and generating output. A computer program includes instructions for a computer to carry out a particular activity to bring about a particular result, and may be written in any programming language, including compiled and uncompiled, interpreted languages, assembly languages and machine language, and can be deployed in any form, including a complete program, module, component, subroutine, or other suitable routine for a computer program.

I claim:

1. An assembly comprising:
   a control system configured to produce a pulsed magnetic or electrostatic field;
   an injectable machine, comprising:
      a body comprising a charge or dipole configured to magnetically- or electrostatically-direct the position of said injectable machine;
      a sub-component device comprising part of said injectable machine, wherein said sub-component device comprises an actuator means for triggering the application of a medicament of said injectable machine by said pulsed magnetic or electrostatic field.

2. The assembly of claim 1, wherein said injectable machine is configured for wireless communications with said control system and wherein said control system is capable of directing activities of said injectable machine.

3. The assembly of claim 2, wherein said control system controls said injectable machine with an external electrostatic and/or magnetic field generating device.

4. The assembly of claim 1, wherein said injectable machine is configured to be delivered by hypodermic needle.

5. The assembly of claim 1, wherein said injectable machine is delivered in a cushioning protective fluid.

6. The assembly of claim 1, wherein said body encompasses or surrounds at least some components of said injectable machine and wherein said body is configured to be released by remotely-issued signaling or by at least one command by a control system.

7. The assembly of claim 1, comprising a control-system-detectable tag incorporated within said injectable machine, and configured for uniquely identifying and locating said injectable tag within a treatment area.

8. The assembly of claim 1, comprising a control-system-detectable tag incorporated within said injectable machine, and configured for uniquely identifying and locating said injectable machine within a treatment area.

9. An assembly comprising:
   a control system configured to produce a pulsed magnetic or electrostatic field;
   an injectable machine, comprising:
      a body comprising a charge or dipole configured to magnetically- or electrostatically-direct the position of said injectable machine;
      a sub-component device comprising part of said injectable machine, wherein said sub-component device comprises an actuator means for creating and powering rotary action of said injectable machine by said pulsed magnetic or electrostatic field.

10. The assembly of claim 9, wherein said injectable machine is configured for wireless communications with said control system and wherein said control system is capable of directing activities of said injectable machine.

11. The assembly of claim 10, wherein said control system controls said injectable machine with an external electrostatic and/or magnetic field generating device.

12. The assembly of claim 9, wherein said injectable machine is configured to be delivered by hypodermic needle.

13. The assembly of claim 9, wherein said injectable machine is delivered in a cushioning protective fluid.

14. The assembly of claim 9, wherein said body encompasses or surrounds at least some components of said injectable machine and wherein said body is configured to be released by remotely-issued signaling or by at least one command by a control system.

15. The assembly of claim 9, comprising a control-system-detectable tag incorporated within said injectable machine, and configured for uniquely identifying and locating said injectable tag within a treatment area.

16. The assembly of claim 9, comprising a control-system-detectable tag incorporated within said injectable machine, and configured for uniquely identifying and locating said injectable machine within a treatment area.

* * * * *